(12) United States Patent
Torsi et al.

(10) Patent No.: US 9,575,029 B2
(45) Date of Patent: Feb. 21, 2017

(54) METHOD TO REALIZE ELECTRONIC FIELD-EFFECT TRANSISTOR SENSORS

(75) Inventors: Luisa Torsi, Bari (IT); Gerardo Palazzo, Mola di Bari (IT); Nicola Cioffi, Bari (IT); Maria Daniela Angione, Bari (IT); Maria Magliulo, Ostuni (IT); Serafina Cotrone, Bari (IT); Gaetano Scamarcio, Bari (IT); Luigia Sabbatini, Bari (IT); Antonia Mallardi, Bari (IT)

(73) Assignees: UNIVERSITA DEGLI STUDI DI BARI, Bari (IT); CONSIGLIO NAZIONALE DELLE RICERCHE ISTITUTO PROCESSI CHIMICO FISICI-IPCF, SEDE DI BARI, Bari (IT)

( * ) Notice: Subject to any disclaimer, the term of this patent is extended or adjusted under 35 U.S.C. 154(b) by 104 days.

(21) Appl. No.: 14/355,100

(22) PCT Filed: Oct. 31, 2011

(86) PCT No.: PCT/IT2011/000364
§ 371 (c)(1),
(2), (4) Date: May 22, 2014

(87) PCT Pub. No.: WO2013/065073
PCT Pub. Date: May 10, 2013

(65) Prior Publication Data
US 2014/0312879 A1      Oct. 23, 2014

(51) Int. Cl.
*H01L 29/786* (2006.01)
*G01N 27/414* (2006.01)
(Continued)

(52) U.S. Cl.
CPC ......... *G01N 27/414* (2013.01); *G01N 27/126* (2013.01); *G01N 27/4141* (2013.01);
(Continued)

(58) Field of Classification Search
USPC .......................................... 257/253, 24, 288
See application file for complete search history.

(56) References Cited

U.S. PATENT DOCUMENTS

2005/0284336 A1* 12/2005 Okada ..................... C09C 1/56
106/476
2011/0095342 A1* 4/2011 Daniel ............. H01L 29/78684
257/288

FOREIGN PATENT DOCUMENTS

EP         2385563 A1     11/2011

OTHER PUBLICATIONS

Ajay A. Virkar et al., Organic Semiconductor Growth and Morphology Considerations for Organic Thin-Film Transistors, Advanced Materials, 2010, vol. 22, pp. 3857-3875, WILEY-VCH Verlag GmbH & Co. KGaA, Weinheim.
(Continued)

*Primary Examiner* — Erik B Crawford
(74) *Attorney, Agent, or Firm* — Heslin Rothenberg Farley & Mesiti PC; Victor A. Cardona, Esq.

(57) ABSTRACT

A transistor includes at least one conductive layer, at least one gate dielectric layer and at least one semiconducting film deposited on top of a receptor molecule layer previously deposited or covalently linked to the surface of the gate dielectric. The layer of biological material includes single or double layers of phospholipids, layers made of proteins such as receptors, antibodies, ionic channels and enzymes, single or double layers of phospholipids with inclusion or anchoring of proteins such as: receptors, antibodies, ionic channels and enzymes, layers made of oligonucleotide (DNA, RNA,
(Continued)

PNA) probes, layers made of cells or viruses, layers made of synthetic receptors for example molecules or macromolecules similar to biological receptors for properties, reactivity or steric aspects.

11 Claims, 5 Drawing Sheets

(51) Int. Cl.
  G01N 33/543 (2006.01)
  G01N 33/00 (2006.01)
  G01N 27/12 (2006.01)
  H01L 29/78 (2006.01)
  H01L 51/00 (2006.01)
  H01L 51/05 (2006.01)
(52) U.S. Cl.
  CPC ..... *G01N 27/4145* (2013.01); *G01N 33/0036* (2013.01); *G01N 33/0057* (2013.01); *G01N 33/5438* (2013.01); *H01L 29/78* (2013.01); *H01L 51/0093* (2013.01); *H01L 51/0512* (2013.01)

(56) References Cited

OTHER PUBLICATIONS

Luisa Torsi et al., A sensitivity-enhanced field-effect chiral sensor, Nature Materials, May 2008, vol. 7, pp. 412-417, Nature Publishing Group.
Yasuhide Ohno et al., Label-Free Aptamer-Based Immunoglobulin Sensors Using Graphene Field-Effect Transistors, Japanese Journal of Applied Physics, 2011, vol. 50, pp. 070120-1-070120-4, The Japan Society of Applied Physics.
Luisa Torsi et al., Contact effects in organic thin-film transistor sensors, Organic Electronics, 2009, vol. 10, pp. 233-239, Elsevier B.V.
Bo Zhang et al., An ultrasensitive and low-cost graphene sensor based on layer-by-layer nano self-assembly, Applied Physics Letters, 2011, vol. 98, pp. 073116-073116-3, American Institute of Physics.
Anatoliy N. Sokolov et al., Fabrication of low-cost electronic biosensors, Materials Today, Sep. 2009, vol. 12, No. 9, pp. 12-20, Elsevier Ltd.
Yat Li et al., Nanowire electronic and optoelectronic devices, Materials Today, Oct. 2006, vol. 9, No. 10, pp. 18-27, Elsevier Ltd.
L. Torsi et al., Multi-parameter gas sensors based on organic thin-film-transistors, Sensors and Actuators B Chemical, 2000, vol. 67, pp. 312-316, Elsevier Science S.A.
Peter Pacher et al., Chemical Control of Local Doping in Organic Thin-Film Transistors: From Depletion to Enhancement, Advanced Materials, 2008, vol. 20, pp. 3143-3148, WILEY-CH Verlag GmbH & Co. KGaA, Weinheim.
Mark E. Roberts et al., Water-stable organic transistors and their application in chemical and biological sensors, PNAS, Aug. 26, 2008, vol. 105, No. 34, pp. 12134-12139, The National Academy of Sciences of the USA.
S.M. Goetz et al., Organic field-effect transistors for biosensing applications, Organic Electronics, 2009, vol. 10, pp. 573-580, Elsevier B.V.
Jun-Yong Sun et al., A graphene-based electrochemical sensor for sensitive determination of caffeine, Colloids and Surfaces B: Biointerfaces, 2011, vol. 84, pp. 421-426, Elsevier B.V.
Arindam Das et al., A Nitrogen Dioxide Sensor Based on an Organic Transistor Constructed from Amorphous Semiconducting Polymers, Advanced Materials, 2007, vol. 19, pp. 4018-4023, WILEY-VCH Verlag GmbH & Co. KGaA, Weinheim.
J.L. Xia et al., Effect of Top Dielectric Medium on Gate Capacitance of Graphene Field Effect Transistors: Implications in Mobility Measurements and Sensor Applications, Nano Letters, 2010, vol. 10, pp. 5060-5064, American Chemical Society.
Alex Dezieck et al., Threshold voltage control in organic thin film transistors with dielectric layer modified by a genetically engineered polypeptide, Applied Physics Letters, 2010, vol. 97, pp. 013307-013307-3, AIP Publishing.
Maria D. Angione et al., Carbon based materials for electronic bio-sensing, Materials Today, Sep. 2011, vol. 14, No. 9, pp. 424-433, Elsevier Ltd.
B. Crone et al., Large-scale complementary integrated circuits based on organic transistors, Nature, Feb. 3, 2000, vol. 403, pp. 521-523, Macmillan Magazines Ltd.
Birendra Singh et al., Bio-organic-semiconductor-field-effect-transistor based on deoxyribonucleic acid gate dielectric, Journal of Applied Physics, 2006, vol. 100, pp. 024514-024514-4, AIP Publishing.
Feng Yan et al., Label-free DNA sensor based on organic thin film transistors, Biosensors and Bioelectronics, 2009, vol. 24, pp. 1241-1245, Elsevier B.V.
International Search Report for International Application No. PCT/IT2011/000364 dated Apr. 20, 2012, 7 pages.

* cited by examiner

METHOD TO REALIZE ELECTRONIC FIELD-EFFECT TRANSISTOR SENSORS

CROSS REFERENCE TO RELATED APPLICATION

This application is a national stage of PCT International Application No. PCT/IT2011/000364, filed on Oct. 31, 2011, and published in English on May 10, 2013, as WO 2013/065073 A1, the entire disclosure of which is incorporated herein by reference.

DESCRIPTION

The object of the present invention consists of innovative methods for realizing field-effect transistors (FET) comprising layers of self-assembled biological systems deposited underneath the semiconductive electronic active material. Furthermore, the present invention relates to the use of said FET devices as label-free, selective and ultra-sensitive sensors for detecting volatile or liquid substances for example of interest, but not limited to, the biomedical field. The semiconductor layer can be selected among p-type and n-type organic or carbon allotrope based material as well as among solution processable inorganic semiconductor. It is required that the semiconductor morphological structure allows the permeation of the analyte all through the film thickness, eventually allowing the probes to reach the receptor molecules deposited underneath the semiconductor. The analyte/receptor molecules can interact both troughs highly specific bio-chemical interaction as well as by means of chemical interactions. The semiconductor can be a carbon based material such as an organic semiconductor (poly(3-hexylthiophene-2,5-diyl), pentacene) but also can be based on carbon allotropes such as, but not limited to, carbon nanotubes and fullerenes. Solution processed inorganic semiconductor such as zinc-oxide or similar materials can be a preferred choice too.

Several sectors in analytical chemistry, such as, for instance food analysis, environmental monitoring and clinical diagnostics, displayed a strong interest toward the development of devices to be directly used in on-field applications. For example, the concept of Point Of Care (POC) analysis refers to the possibility to perform diagnostic procedures, in an accurate and rapid way, directly at the place where they are needed (doctor's office or the hospital). The analytical systems for such applications must be easy to use and capable to provide easily readable outputs/responses as well as quantitative data. In this respect, biosensors being capable to perform fast analysis and label-free detection, have been proven to be very promising since they are able to directly probe a biological recognition event without the need of a marker. Recently, attention was directed to the development of immunosensors and genosensors offering a fast, continuous and in situ detection as well as a quantification of analytes in complex matrices such as blood. Such biosensors exploit specific immunologic (antigen/antibody binding) or nucleic acid hybridization (binding of complementary sequences) reactions for identification and quantification of analytes, using a proper transduction signal which can be an optical, electrochemical, or electronic one. In particular, immunosensors, in comparison to other analytical methods, present the following advantages:—are selective and sensitive;—can be used for on field analysis;—can be fully automated;—their response can be fast and the analytes do not need usually to be purified or treated before the analysis. However, a lot of up to date developed biosensors present disadvantages in terms of cost, reagents availability, regeneration and reproducibility. Moreover, the sensor sensitivity is markedly influenced by the transduction mechanism and only few satisfactory performing biosensors are available on the market. One of the major open issues being as yet:—sensitivity;—capability to allow a quantitative analysis;—possibility to fully integrated the sensor into an electronic circuit. Hence, the need arises to have fast, reliable, accurate, miniaturised and low cost biosensors.

Although presently only some preliminary studies have been performed, Field—Effect Transistors (FETs) present interesting characteristics to be successfully employed as label-free biosensors. This is mostly due to the possibility to implement such devices in high performance portable detection systems. One of the sensor market major requests is the possibility to have devices capable of detecting, biological and chemical analytes, on-line and in situ. Such devices could be employed in a wide range of applications ranging from food and beverage control, to medical diagnostic and public security. Such requirements are not still completely fulfilled by the technology supporting the sensors currently on the market. The selectivity, the capability to work at room temperature and the high sensitivity to a wide range of analytes are still open issues in the field and, in this respect, FETs have shown the capability to overcome some of these limits. In this respect FET devices based both on organic, carbon based as well as inorganic active layer materials have been so far proposed mainly as nanostructured systems [L. Torsi, A. Dodabalapur. "*Organic Thin-Film Transistors as Plastic Analytical Sensors*" Anal. Chem., vol 77 (19), pp 380-387, 2005; N. A. Sokolov, M. E. Roberts, Z. Bao. "*Fabrication of low cost electronic biosensors*", Materials Today, vol. 12, pp. 12-20, 2009; M D. Angione, R. Pilolli, S. Cotrone, M Magliulo, A. Mallardi, G. Palazzo, L. Sabbatini, D. Fine, A. Dodabalapur, N. Cioffi and L. Torsi. "*Organic bio-electronic sensors*" Materials Today 14 (9), 424-433 (2011); Li Yat; Qian Fang; Xiang Jie; et al. "*Nanowire electronic and optoelectronic devices*" Materials Today 9 (10) 18-27 (2006). In particular Organic-FETs have been shown to work as multi-parameter sensors, displaying a high repeatability, a fast and reversible response. They are also capable to work at room temperature with a good selectivity toward a wide range of analytes, and allow on-state analyte detection and amplified sensitivity as the applied gate bias is increased [L. Torsi, A. Dodabalapur, L. Sabbatini, P G: Zambonin. "*Multi-parameter gas sensors based on organic thin-film-transistors.*" Sens. Actuators B. vol 67 (3) pp 312-316, 2000; L. Torsi, F. Marinelli, M D Angione, A. Dell'Aquila, N. Cioffi, E. De Giglio, L. Sabbatini. "*Contact effects in organic thin-film transistor sensors*". Organic Electronic. vol. 10 (2) pp 232-239 2009]. Furthermore, the bilayer architecture FET sensor, recently proposed, appears to be of great interest for high performance analysis of chiral analytes [L. Torsi, G M Farinola, F Marinelli, M C Tanese, O Hassan Omar, L Valli, F Babudri, F Palmisano, P G Zambonin, F Naso. "*A sensitivity-enhanced field-effect chiral sensor*", Nature Materials, vol. 7, pp. 412-417, 2008]. The bilayer structure has been engineered combining field effect transistors with chiral recognition properties, allowing a differential enantiomeric detection of volatile analytes at unprecedented low concentration, namely in the ppm range. Biological recognition measurements are usually performed in aqueous media and low voltage transistors are able to assure stable working conditions in such an environment. Water electrolysis and high ionic analyte conductivity represent, indeed, the main drawbacks to overcome for applications in an aqueous environment. New organic and inorganic dielectrics have been recently developed to lower FET threshold bias and to invert the slope below the threshold voltage, both responsible for the high FET voltages [M. E. Roberts, S. C. B. Mannsfeld, N. Queraltó, C. Reese, J. Locklin, W. Knoll, Z. Bao. *Water-stable organic transistors and their application in chemical and biological sensors. PNAS* vol. 105 (34), pp. 12134-12139, 2008]. Such figures of merit depend also on gate dielectric properties. This implies the development of high capacity thin gate dielectrics, one of the main challenges of flexible and organic electronics.

Interesting is also the more recently proposed grapheme materials for electronic and electrochemical field-effect transistor sensors (Xia J. L.; Chen F.; Wiktor P.; et al. "*Effect of Top Dielectric Medium on Gate Capacitance of Graphene Field Effect Transistors: Implications in Mobility Measurements and Sensor Applications*" NANO LETTERS 10(12) 5060-5064 (2010); Zhang Bo; Cui Tianhong "*An ultrasensitive and low-cost graphene sensor based on layer-by-layer nano self-assembly*" APPLIED PHYSICS LETTERS Volume: 98(7) Article Number: 073116 (2011); Sun Jun-Yong; Huang Ke-Jing; Wei Shuai-Yun; et al. "*A graphene-based electrochemical sensor for sensitive determination of caffeine*" COLLOIDS AND SURFACES B-BIOINTERFACES 84 (2) Pages: 421-426 (2011); Ohno, Yasuhide, Maehashi, Kenzo, Inoue, Koichi, Matsumoto, Kazuhiko" *Label-Free Aptamer-Based Immunoglobulin Sensors Using Graphene Field-Effect Transistors, JAPANESE JOURNAL OF APPLIED PHYSICS* 50 (7) Article Number: 070120 (2011).) This is also an interesting option as graphene has a field-effect mobility that is generally higher than that of organic semiconductor and is also solution processable and potentially printable. It holds also a not compact morphology specifically when processed from.

The immobilization of biomolecules, such as DNA, enzymes or other proteins, on sensor surface represents a new basic research area involving different interdisciplinary fields. The development of new structures which are capable to provide a direct link between the complex world of biology and digital electronics is a target of scientific research worldwide. The choice of the method of bio-probe immobilization allowing a specific biomolecule to retain its biological function is one of the most important aspects in biosensor fabrication. To obtain a bio-recognition reaction which is selective, sensitive and reproducible, it is necessary to immobilize the biomolecules on the active surface to obtain well oriented molecular layers. Furthermore, to increase sensitivity it is essential to minimize the distance between the transduction surface (the electronic channel in case of e FET device) and the layer of immobilized biomolecules.

The biomolecules can be immobilized on a sensor surface in different ways. For immobilization purpose, several materials can be used such as for instance nafion, sol-gel, lipid membranes, conductive polymers, organic or inorganic semiconductors as well as self-assembled monolayers (SAM). SAM are particularly suitable as biosensor active layer since they form thin, ordered and stable monolayers and they can be grafted on the surface thanks to the wide availability of head-groups. Furthermore, they can provide to biomolecules a microenvironment similar to that of the membranes and require only minimal quantities of often very expensive biomolecules. Another alternative method consists in the use of electrosynthesized conductive polymers as matrices for immobilizing bio-components. From the scientific literature and in particular as a consequence of the important work of the researchers Foulds and Lowe published in 1988, the immobilization of biomolecules such as enzymes, DNA, antibodies and even whole cells in conductive polymers was studied for manufacturing biosensors, including immunosensors. Among conjugated polymer, polypyrrole (PPy) and poly(3-hexylthiophene) (P3HT) can be considered one of the most interesting materials for their excellent semiconducting properties, stability and biocompatibility. In addition to PPy and its derivatives the use of conductive polymers such as poly(aniline), poly(3-hexylthiophene), poly(o-aminobenzoic acid) has been studied for the realization of chemical and biological sensors. Recently attention has been directed to the use of systems mimicking cell membranes for immobilizing biomolecules. The low bioactivity of membranes renders them particularly interesting as an interface between the not biological material on sensor surface and biologically active fluids. Lipid membranes represent also a natural environment for biological molecules. Thanks to the natural environment, it is possible to prevent biomolecule denaturation and to obtain high sensitivity and selectivity. Furthermore, low membrane bioactivity prevents signal interferences, while active biomolecule localization on a surface favours signal transduction. The membranes can be deposited on a surface in several ways. In particular, sensor surface can be modified introducing binding sites specific for lipid molecules to deposit the membranes in a more steadily manner. The sensor configuration here proposed combines the high selectivity of a bio-recognition element with the high sensitivity typical of the electronic transduction offering high analytical performances. Such a label-free FET sensor does not require large sample volumes, involves minimal sample pre-treatment and low reagent consumption, along with the elicited high specificity and sensitivity. Furthermore, in principle, even the analysis of complex matrices can be performed with miniaturized and automatized arrays implemented in portable and disposable devices. In this respect the work already performed on the realization of a technology based on the integration of p-type and n-type organic FETs into a flexible array for electronic product purposes (Crone B, Dodabalapur A, Lin Y Y, Filas R W, Bao Z, La Duca A, Sarpeshkar R, Katz H E, Li W "*Large scale complementary integrated circuits based on organic transistors*" NATURE vol. 403, 521-523, 2000) could be borrowed and adapted to realize a cheap and disposable sensing array.

Important to note is that a device configuration presenting a layer of a biological recognition system deposited between the dielectric and the semiconductor, which represents the peculiarity and the innovation of this specific patent, have never been proposed before. The major advantage is that such a configuration allows a intimate contact between the recognition bio-layer and the two dimensional charge transport occurring in the FET incrementing, as it will be shown further on, by orders of magnitude the device sensitivity.

All devices object of the present invention can function as electronic sensors and can be realized by techniques developed in the framework of flexible or organic electronics. The main advantages are:

- FET sensors allow label-free detection; in fact it is not necessary to label the sample by attaching fluorescent or electro-active markers to the species to be analysed;
- single devices, as well as matrix systems (array), are miniaturizable and realizable with low cost screen-printing or other printing compatible technologies, on substrates made of plastic, paper or even fabrics;
- electronic FET sensors do not need a reference electrode (generally necessary to electrochemical sensors) to measure the current changes induced by the interaction with the species to be detected.

Currently available sensors for the suggested detections, for example those with optical or electrochemical detection, fail to fulfil at least one of the above listed characteristics.

The herein proposed sensor allows to probe enzymatic, hybridization and immunochemical reaction, protein-protein, protein-ligand and cellular interactions and specific cellular signal transduction events. The transistor sensor can be used in a procedure comprising the following steps:
a) presence of at least one field-effect transistor available;
b) bring in contact the analyte (gaseous/vapour or liquid) with the transistor by directly exposing the device channel to the analyte;
c) measure of the variation of at least one electrical, electrochemical or capacitive quantity as a response of the transistor to a reaction or to a recognition event involving the receptor layer and the analyte molecule. Accordingly, the measure of the variation in the step c) is that of the electrical conductivity, the channel electrical resistance, the density of charge carriers and the capacitance between the gate electrode and the channel region.

These and other advantages will be better highlighted in the detailed description of the invention which specifically refers to tables 1 and scheme 1, FIGS. 1 to 8, in which an example absolutely not limiting of a preferred realization of the present finding is exposed. In particular.

Figure 1:
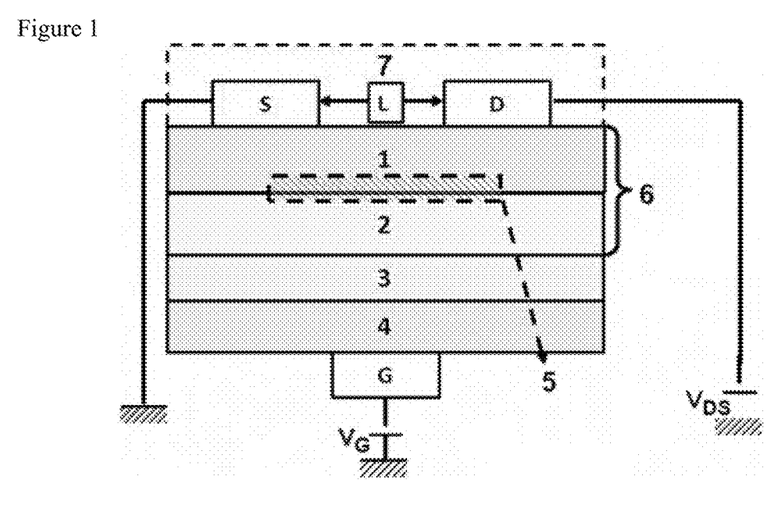
FIG. 1 shows the FET sensor structure made of an active material comprising a biological layer of type (a), (b), (c), (d) or (e), as reported in detail at page 11, covered by an organic semiconductor, for example, but not limited to, poly-3-hexyl-thiophene; other carbon allotropes based as well as inorganic semiconductors can be used as well. In the figure the semiconductor S (1), the self-assembled biological layer SBL (2), the dielectric (3), the conductive substrate (4), the channel region (5), the active material (6) and the analyte (7) are displayed.

The devices described in the present finding have a structure of a field effect or similarly of a thin-film transistor (FET) as displayed in FIG. 1. The transistor is fabricated starting from an highly doped silicon substrate (resistivity 0.02-1 Ohm/cm) acting as gate material. It is also possible to use a metallized glass slide a highly doped silicon or a flexible plastic substrate but also paper or fabric substrate. In the present case the doped silicon wafer is covered by a $SiO_2$ layer (thickness 100 nm or 300 nm) acting as a dielectric. The suggested procedures can be readily extended also to other oxides such as $TiO_2$ or polymeric dielectrics provided that they are properly treated in order to hold —OH type functionalities allowing the anchoring of the biological layer. Dielectric thickness and material dielectric constant determine the bias necessary to operate the device. In the exposed case bias are as high as −100 V (−40 V for 100 nm thick $SiO_2$) but examples in literature show that FETs, also used as sensors, can be operated at bias lower than 1 Volt (M. E. Roberts, S. C. B. Mannsfeld, N. Queralto, C. Reese, J. Locklin, W. Knoll, Z. Bao. *Water-stable organic transistors and their application in chemical and biological sensors.* PNAS vol. 105 (34), pp. 12134-12139, 2008; Das Arindam; Dost Rene; Richardson Tim; et al. "*A nitrogen dioxide sensor based on an organic transistor constructed from amorphous semiconducting polymers*" ADVANCED MATERIALS vol. 19(22, 4018, 2007). Before device fabrication, a cleaning step of the dielectric surface is always performed, it includes: washing in $H_2O$, followed by washing in acetone and again $H_2O$; sonication in isopropanol for 10 minutes; sonication in methanol for 10 minutes; again $H_2O$—acetone—$H_2O$. It is generally convenient to perform a washing treatment with solvents at increasing polarity and even a treatment with oxygen plasma followed by an activation step of the oxide, aimed at increasing the number of polar groups (—OH) on substrate surface. This last step is performed using a solution composed of sulphuric acid and hydrogen peroxide (piranha) or UV treatment with ozone. The innovative aspects of the device, object of the present patent is the presence of a biological layer deposited directly on the dielectric surface. The possible biological systems include:
(a) single or double phospholipidic layers;
(b) layers composed by proteins such as: receptors, antibodies, ionic channels and enzymes;
(c) single or double phospholipidic layers with inclusion or anchoring of the proteins listed at point (b);
(d) layers composed by oligonucleotide (DNA, RNA, PNA) probes;
(e) layers composed by cells or viruses;
(f) layers composed by synthetic receptors (molecules or macromolecules similar to biological receptors for properties, reactivity or steric aspects).

Biological systems can be covalently bound or otherwise adhered (physical adsorption, spin-coating) to the dielectric.

A semiconductor, such as for example oligomers or polymers of thiophene, also substituted with alkyl chains, oligoacenes such as pentacene, tetracene or anthracene, phthalocyanines, porphyrins but even naphthalenes, or carbon allotropes such as, but not limited to, carbon nanotubes and fullerenes, is deposited on top of the deposited biological layer. Inorganic semiconductors such as ZnO are considered as well. In fact printable semiconducting materials are the preferred choice in this invention. Indeed, both p and n-type semiconductors can be used and deposited by means of printing compatible procedures, such as spin-coating or drop-casting in case of soluble materials or by thermal evaporation in case of not soluble materials. In this specific case the semiconductor p-type and it is deposited by spin-coating. Specifically the poly(3-hexylthiophene-2,5-diyl-P3HT) (Sepiolid P 200, supplied by Basf) was dissolved in chloroform at a concentration of 2,6 mg/ml. The commercial material was purified following a procedure of subsequent washing in a soxhlet apparatus with methanol and hexane. The deposition of purified P3HT was performed by spin-coating at a spin rate of 2000 rpm 30 sec long.

Figure 2:
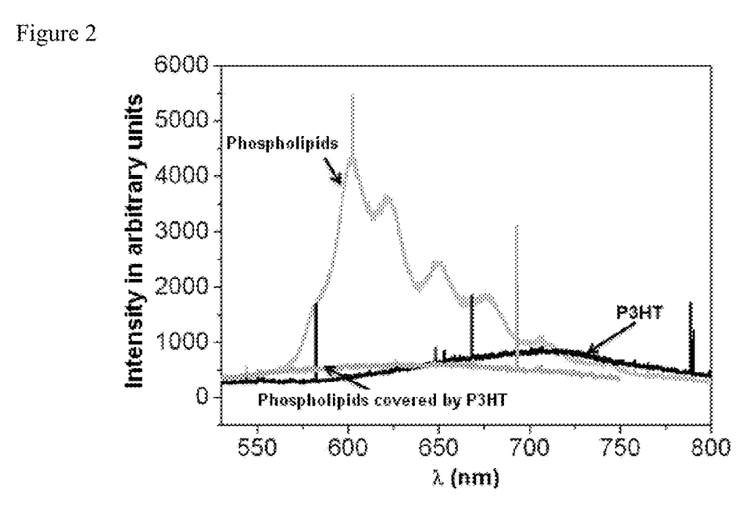
FIG. 2 shows the curve of the micro-luminescence spectra of a phospholipidic layer, properly labelled with Texas-Red fluorophore, the P3HT and the multilayer made of phospholipids on which P3HT was deposited. Both the phospholipidic and the P3HT layer were deposited by spin-coating.

This patent proposes, for the first time, an FET comprising a biological layer directly at the interface with the channel region. This configuration has the capability to provide an FET device with better electronic properties and higher performances, particularly in terms of sensitivity, since the recognition event of the analyte takes place where the bi-dimensional charge transport (field-effect) responsible of current amplification. The device structure is shown in FIG. 1. All the deposited biological layers, as well as all the active multilayers (meaning the biological layer covered by the semiconductor), underwent an extensive surface and volume spectroscopic characterization. Surface characterization was performed through X rays photoelectronic spectroscopy (XPS), used in conventional, angle resolved (ARXPS), and imaging (map-scan XPS) mode. The first operative mode was employed to get general information about the composition and chemical speciation of the surface. The ARXPS mode was used as a not destructive study of element and functional group distribution in a thin layer corresponding to about 5 nm of the most external surface portion. Further, ionic controlled erosion (ion-beam assisted depth-profiling XPS) was adopted to explore layers of higher thickness. In both cases for the reconstruction of the concentration profiles, target elements, such as phosphorus, sulphur, nitrogen, were chosen to identify the presence of single multilayer component and an advanced XPS data analysis software was subsequently employed to obtain the elicited profiles. Finally, the analysis performed in imaging-XPS mode with a resolution corresponding to about 20 μm, allowed to verify the uniformity of the multilayers surface. Volume characterization was performed too by micro-luminescence technique on both the single P3HT and on the multilayers. As an example the case of the sample including the phospholipidic layer is reported. FIG. 2 shows the luminescence spectra excited with the 476 nm line of a Kripton laser.

Figure 3:
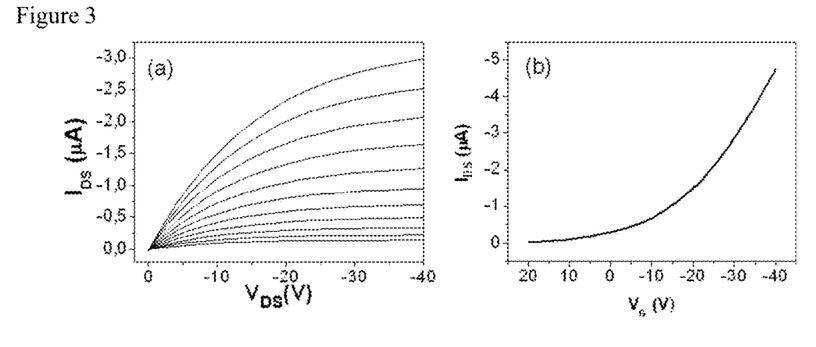
FIG. 3 shows: (a) the curves of the current-voltage characteristics (IDS vs. VDS at different VG values) of a P3HT FET; (b) transfer characteristics of the same device (IDS vs. VG at VDS=−30 V)

In such FIG. 2 the micro-luminescence spectra of just the phospholipids film deposited through spin-coating from an aqueous solution (further details are reported in the section dedicated to example 1) are compared; this spectrum is particularly intense since fluorophore (Texas-Red) labelled phospholipids have been used. A luminescence signal can be recorded also for the bare P3HT film, even though less intense and red shifted. The characterization proceeded with the measurement of a sample fabricated by depositing the phospholipidic layer covered by a P3HT layer: This latter layer was deposited by spin-coating from a chloroform solution (example 1). It is evident that the luminescence line shape of the phospholipidic layer covered by the semiconductor, shows contributions from both the phospholipid and the semiconductor staking layers. This confirms that P3HT deposition does not remove the biological layer deposited underneath. This is a critical information that supports the interpretation of the results, shown in the following, obtained using this system as a sensor. The structure was confirmed also by morphological measurements performed by atomic force scanning microscope. Manufacturing of FET device was then completed by depositing the source (S), drain (D) and gate (G) contacts by thermal evaporation ($8 \times 10^{-7}$ torr) of gold through a shadow mask. This method of FET manufacturing is compatible with screen-printing or other printing compatible technologies allowing device realization, even in array configuration, at low cost and allows implementing them on plastic, paper or even fabric substrates. The source (S) drain (D) and gate (G) contacts in the transistor structure-can be deposited by thermal evaporation or sputtering of gold or other metals such as platinum, silver or aluminium through a shadow mask or defined by photolithographic techniques. The contact electrodes can be also made of a conducting polymer material such as poly(3,4-ethylenedioxythiophene) poly(styrenesulfonate) or of a conducting ink made of metal nano-dispersions. The geometry used to define the S and D contacts results in rectangular pads that can be spaced by 1 to 500 μm; this spacing is addressed as "L" (FIG. 1) being the channel length. The S and D contacts can be also be deposited directly on the the dielectric layer just after surface cleaning procedure. The device is operated in the common source configuration. Because of the capacitive coupling effect between dielectric and active material (performed by biasing the gate contact respect to the grounded source), it is possible to tune the current passing between source and drain. The charge induced by the gate field is confined, because of field-effect, to a bi-dimensional region, called in fact the channel region, at the interface with the dielectric. FET devices, including a biological active layers as reported in FIG. 1, were used as sensors at first by measuring the electrical behaviour of the device composed of the sole P3HT film. Typical current voltage characteristics (I-V) are reported in FIG. 3. In particular FIGS. 3(a) shows the I-V characteristics obtained measuring the IDS current flowing between S and D as a function of the VDS bias at different gate biases, VG. In FIG. 3(b) the IDS current curves as a function of VG bias at constant VDS (−40 V) are reported. Such curves are called transfer characteristics. The data analysis, performed according to consolidated procedures results for the device in FIG. 3 in a field effect mobility, μFET, of $5 \times 10^{-3}$ cm$^2$/Vs, Ion/Ioff=10, and threshold voltage, Vt, of 7 V.

Figure 4:
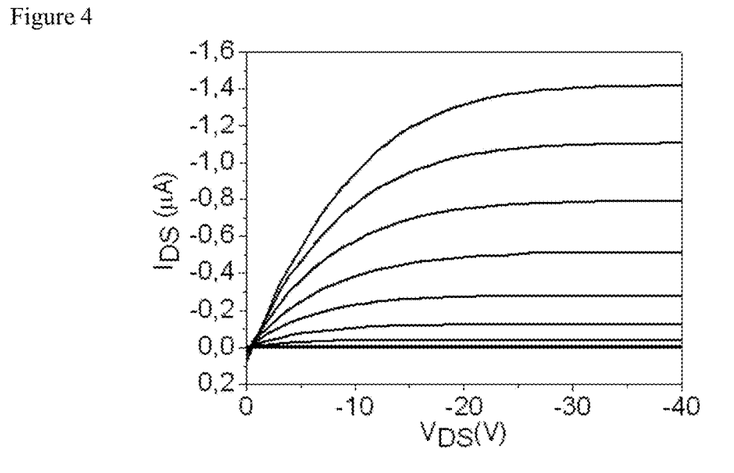
FIG. 4 shows the curves of current-voltage characteristics of an FET made of a phospholipidic layer covered by a P3HT layer.

The current-voltage characteristics of an FET, fabricated depositing a P3HT layer on top of a phospholipidic layer as previously described are reported in FIG. 4. It is interesting to note that also the device including the phospholipid layer covered by the P3HT films works beautifully as transistor. In particular, μFET, of $6.25 \times 10^{-3}$ cm$^2$/Vs, Ion/Ioff=100, which is in line with the best performing P3HT devices [A A. Virkar, S. Mannsfeld, Z. Bao, and N. Stingelin. *Organic Semiconductor Growth and Morphology Considerations for Organic Thin-Film Transistors. Adv. Mater*, vol 22, pp 3857-3875, 2010]. Even more striking is the fact that figure of merits such as the amplification ratio (Ion/Ioff), even improved with the introduction of the phospholipidic layer.

It is the first time that an FET comprising a biological layer at the interface between the semiconductor and the gate dielectric is realized and proven to work at such high level of performances. In this case the electronic characteristics are even better for the FET comprising the biological layer.

Both the bare P3HT FET devices as well as the FET comprising the multilayer (including the biological layer as in FIG. 1) were then exposed to the analyte. For both devices the transfer characteristics were measured upon exposure of the channel region to the analyte to be detected. The transfer characteristics current changes before and after the exposure is taken as the sensor response. Furthermore, ad hoc designed control experiments (blank measurements) were performed as described in details in the examples reported (vide infra). To perform the sensing experiments, different procedures were used for the detection of volatile and liquid substances.

Procedure 1: Determination of Volatile Analytes

A controlled concentration flow of the analyte was obtained by bubbling the inert carrier gas, $N_2$, into two bubblers containing the analyte in its liquid form. This allows to obtain a nitrogen flow having a partial pressure of the analyte vapours equal to the pressure of saturated vapour of the same analyte at the working temperature of the analysis. To increase the saturation efficiency, besides the trap, the two bubblers were used in series. The temperature was controlled and kept constant by dipping the bubblers in a cryothermostat. Flow control is achieved through a system of two computer controlled flowmeters (Brooks Smart DMFC model 5850C). The described experimental apparatus, allows to control independently and simultaneously the flow of the carrier gas and that of the nitrogen saturated with the analyte. Analyte concentrations sent on the sample can be changed with subsequent dilutions obtained by changing the rate of the two flows.

Procedure 2: Determination of Bio-Analytes in Water

To perform the bio-sensing measurements in water, the solution containing the analyte was deposited directly on the semiconductor and incubated long enough to allow both the diffusion of analyte through the semiconductor layer and the binding with the element deputed to biological recognition. Subsequently, the not bound excess analyte was removed by washing and the device was dried under a nitrogen flow.

Examples of realizations of two specific FET sensors used for different applications are reported in the following:

EXAMPLE 1

Manufacturing and Functioning of Sensor 1

In this case, the FET was realized using phospholipids layer as biological system. This device is proposed as a sensor for anaesthetics. The device sensitivity to anaesthetic substances such as halothane and diethyl-ether resulted an order of magnitude higher than that to other vapours, with the same volatility, such as acetone or isopropanol. This is particularly interesting also because it is very difficult to selectively detect substances with the same volatility by means of a chemical sensor.

Figure 5:
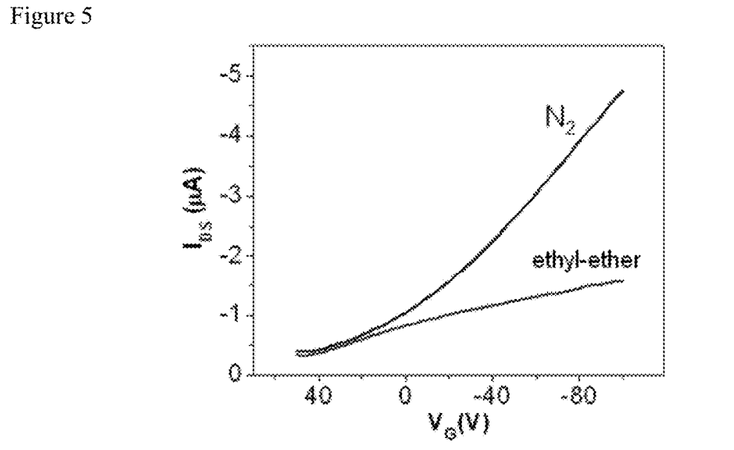
FIG. 5 shows the transfer characteristics curves of sensor 1 exposed to an inert gas ($N_2$) atmosphere and to ethyl-ether. Sensor response is defined by the difference between IDS values (measured in $N_2$ and in the analyte atmosphere) at a fixed VG potential.
Figure 6:
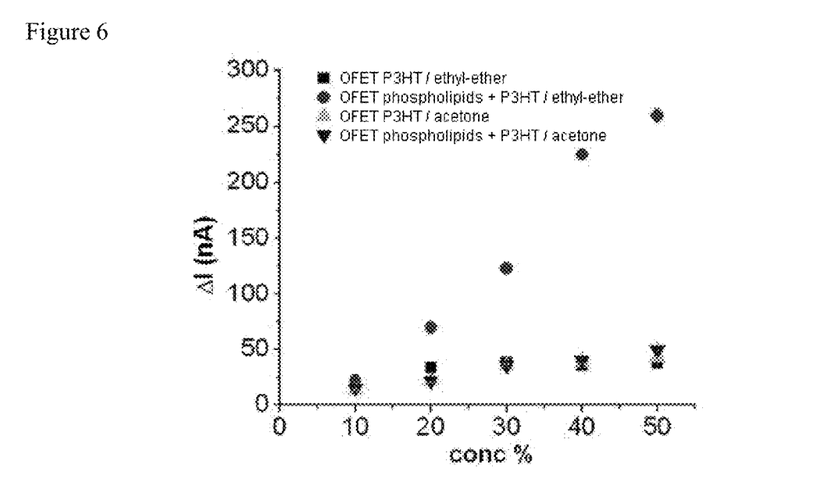
FIG. 6 shows the graph of the calibration curve of sensor 1 and the control device (P3HT FET) exposed to a controlled atmosphere of ethyl-ether or acetone. Each data point is the result of three measurements and the error bars are the mean standard errors.

The device was realized as follows. A layer of phospholipids was deposited, on a properly washed and treated $SiO_2$ surface, by starting from an aqueous suspension of single unilamellar vesicles (SUV). The suspension was realized dissolving 10 mg of soybean lecithin (EPIKURON 200, Cargill) in chloroform allowed to evaporate under vacuum, afterword. The phospholipids were suspended in 1 ml of distilled water and sonicated on ice for 30 minutes. Then, the obtained multilamellar vesicles suspension was repeatedly subjected to extrusion using a polycarbonate filter having pore sizes of 100 nm, to obtain evenly dimensionally distributed unilamellar phospholipidic vesicles. 50 µl of this solution were deposited on the Si/$SiO_2$ substrate, subjected then to a rotation of 200 rpm for twenty minutes. Similarly but on a different device, also a film known as "purple membranes" constituted by the bacteriorhodopsin membrane protein and lipids was deposited. Even in this case, the deposition was performed by spin-coating from a "purple membranes" suspension in $H_2O$. Atomic force scanning micrographies (AFM) show how such spin coating procedure at a very slow rotation results in a multilayer of phospholipids made of flat surfaces with a very smooth and even surface. P3HT is subsequently deposited again by spin-coating but from chloroform directly on the phospholipidic film as well as on the "purple membranes". The measurements reported in FIG. 2 show that the deposition of the semiconductor does not remove the phospholipidic film. AFM measurements evidenced in fact that the phospholipidic layer deposited by spin coating from water is not removed when bare chloroform is spun over it. The result of such an experiment is a drastic reduction of thickness which goes down to few nanometer and the surface becomes much more even and extremely flat. The comparison between the transfer characteristics of sensor 1 exposed to an inert gas ($N_2$) and to a flow of 40% ethyl-ether in $N_2$ is outlined in FIG. 5. It is evident that ethyl-ether causes a remarkable decrease of the current flowing in the channel region. Similar results were obtained with an anaesthetic still in use such as halothane. In this case the measured responses are in the range of clinical concentrations (2-4% in $N_2$) useful for real applications. An even higher and opposite sign response was obtained substituting the simple phospholipidic layer with a "purple membranes" which is known to contain in addition to phospholipids also bacteriorhodopsin. In fact, in this case the exposure to the anaesthetic causes a current increment. Being P3HT a p-type semiconductor the current increment is to be ascribed to the injection of $H^+$ ions in the bidimensional transport region of the transistor, as it is foreseen by the conformational change of bacteriorhodopsin. This result is particularly remarkable since it demonstrates how it is possible to integrate a membrane protein in an FET to build a sensor. But it is even more important that the protein continues to work and the transistor allows performing an electronic detection of a conformational change. The calibration curves of sensor 1, containing just the phospholipidic layer, when exposed to both ethyl-ether and another vapour of comparable volatility (acetone) are shown in FIG. 6. The response $\Delta I$ reported on the abscissa is the change of IDS following the exposure to the analytes vapours respect to the value in $N_2$. Both values are taken at VG=−40 V. For comparison, an FET with only P3HT was exposed to the same substances. The calibration curves of FIG. 6 evidence how the response to ethyl-ether is about a factor 10 higher for the FET including the phospholipidic layer respect to the control device. Instead, it is interesting to note that the exposure to acetone vapours does not cause an important effect neither in sensor 1 and nor in the control device. It is also interesting to observe that exposure of the same devices to an alcohol such as isopropanol displayed a similar behaviour to that of acetone. The response of the P3HT FET to isopropanol is slightly higher than foreseen probably because of the swelling effect of the semiconductor favoured by interactions between the alkyl chains. A similar effect has been already proven in the past. The mechanisms by which molecules such as ether, halothane, desflurane or nitrogen protoxide, are able of induce a state of general anaesthesia are not, as yet, fully understood. One of the most accredited theories however foresees the involvement of just the interactions between the anaesthetic molecules and cell membranes even if it is not clear if the presence of any specific receptors is required. Although these studies evidence the peculiarity of the interactions between anaesthetics and membranes, it was never thought before to employ a phospholipidic bilayer as an active material in a sensor for such substances. A sensor with a thin film transistor (TFT) configuration is particularly suitable to the aim, not only for the already proven high sensitivity, but mostly because it exploits an interface phenomenon, such as the field effect, to induce the electronic response. The synergic effect of these two factors, coupled for the first time in a sensor, generates a device potentially useful for monitoring anaesthetic substances with an interesting degree of selectivity, good sensitivity and excellent reproducibility. The low manufacturing costs and the possibility to miniaturize the devices based on a soluble carbon based or inorganic semiconductors are further advantages of the system object of this patent. The methods adopted for the realization of sensor 1 can be readily extended to the realization of a sensor comprising the biological system (c) which includes any one of the proteins of which at point (b) or (f). The realization procedure of the device foresees the deposition of double phospholipidic layers which includes membrane proteins (such as receptors, ionic channels or enzymes of different kind), starting from proteoliposomes, or better vesicles containing in the double lipid layer the proteins of interest. Proteoliposomes are prepared by molecular exclusion chromatography (micelles mixed with phospholipids, detergent and protein in proper ratios, are filtered on Sephadex G-50 columns) and are subsequently deposited on the dielectric layer of the device. It is widely reported in literature that, after deposition on a solid substrate, spontaneous melting of the vesicles occurs simultaneously to adsorption of the double layer on the substrate. The case of "purple membranes" previously discussed is only one of the possible examples. In presence of soluble proteins such as antibodies the deposition strategy foresees anchoring of the protein to a double lipid layer deposited as previously described. But in this case, lipids functionalized with amino or carboxylic groups to which the antibody can be covalently bound through bioconjugation procedures reported in literature and employing the EDC/Sulpho-NHS system have to be used.

EXAMPLE 2

Manufacturing and Functioning of Sensor 2

In this case the FET sensor was fabricated using the streptavidin-biotin system as model. Streptavidin was immobilized on the dielectric layer by physical adsorption, spin-coating and chemical binding. The fabrication steps of the biomolecule immobilization on the OTFT sensor surface are reported in the following. The procedures optimized for the specific reported case of streptavidin can be readily extended to FETs realized with the other protein classes mentioned at point (b) as well as with biological systems reported at points (d) and (e) and from synthetic receptors as reported at point (f). The extension to other carbon or inorganic based semiconductors is also foreseen.

Immobilization of streptavidin by physical adsorption was performed incubating the $Si/SiO_2$ substrates, previously washed and activated, with a streptavidin solution in phosphate buffered saline 0.01M pH 7.4 (PBS) overnight at room temperature. The substrates was then washed with water and saturated with a solution containing BSA 1% in PBS for 2 hours. After washing with water the devices were dried under nitrogen flow and used for the semiconductor deposition. Concentrations of streptavidin in the range 1-100 µg/ml were used to optimize capture protein immobilization. Immobilization of streptavidin by spin-coating was achieved by depositing a solution of streptavidin in water on $Si/SiO_2$ substrates, previously washed and activated, at a rate of 200 rpm until evaporation of the solvent was complete. Concentrations of streptavidin in the 1-100 µg/ml range were used to optimize capture protein immobilization. For the streptavidin chemical binding the washed and activated devices were functionalized with a 5% solution of 3-aminopropyl-trietoxysilane (APTES) in ethanol. The functionalized devices were then treated with a 2.5% glutaraldehyde solution in PBS and subsequently, in order to obtain the binding of the protein, they reacted with a streptavidin solution in PBS. Next, optimization of capture protein immobilization is performed through luminescence imaging. The homogeneity of the immobilized biomolecule layer on sensor surface and the effect of organic solvents such as chloroform, used for deposition of the semiconductor on the protein layer, were valued by means of luminescence imaging techniques using the streptavidin—Alexa Fluor 488 fluorescent conjugate. The fluorescence images were acquired using a fluorescence microscope equipped with a CCD camera. The devices, on which protein recognition elements were immobilized, were subjected first to fluorescence analysis and subsequently to treatment with an organic solvent. The homogeneity of the deposited protein layer was evaluated by taking fluorescence images acquired for each immobilization procedures and for each concentration. Furthermore, the fluorescence images were acquired before and after treatment with chloroform to evaluate if the treatment with organic solvents (used for the deposition of the semiconductor on the biomolecule layer) modifies the structure of the immobilized protein. The images obtained by different immobilization techniques shows that the best results are obtained immobilizing the protein molecules through the spin-coating technique and chemical binding. In fact, a homogeneous protein layer is obtained with these two techniques and small covering imperfections are observable only at very high magnifications. Instead, in the case of immobilization by physical adsorption some inhomogeneous areas and dielectric portions not covered by the protein layer can be observed, even ay low magnifications. Such observations were also confirmed by electric measurements, in fact, the devices obtained by physical adsorption of the protein exhibited worse electric parameters. Concerning the protein concentration, in all cases, the best results were obtained using a concentration of 10 µg/ml. Such concentration is enough to assure an excess of capture protein so that all antigen molecules can react. Furthermore, working in excess of capture reagent assures that significant signal changes are not observed even in the case of small changes of protein immobilization efficiency. Furthermore, it must be pointed out that a fundamental aspect in the deposition of protein molecules on the dielectric layer hydrophilicity. Tests performed on devices not activated or made hydrophobic by treatment with hexamethyldisilazane (HMDS) showed an insufficient and inhomogeneous deposition of the protein layer. For all protein deposition methods, the fluorescence images obtained after treatment with chloroform highlighted that treatment with the organic solvent does not change the structure of the immobilized protein layer.

Analyte capability to pass through the layer of deposited semiconductor on the biological recognition element as well as the immobilized protein keeping its biological functionality were devalued by chemi-luminescence reinforced by immobilizing the horseradish peroxidase enzyme (HRP) and the chemiluminescence system constituted by luminol/$H_2O_2$/p-iodophenol. The choice of the chemi-luminescence technique was driven by the fact that luminol has a size comparable to that of biotin, then the development of light can be obtained only if this, or the other components of the substrate, pass through the semiconductor layer and if the HRP enzyme remains active. To perform the determination, a 100 µg/ml HRP solution in water was deposited by spin-coating on the washed and activated device $SiO_2$ surface. After enzyme immobilization, the semiconductor was deposited and finally the chemi-luminescence substrate was added. Chemi-luminescence images were immediately acquired by a CCD camera. As a result of the chemi-luminescence substrate addition it would be possible to observe a light signal only if the enzyme remains active and if the substrate components reach the immobilized enzyme passing through the semiconductor.

The chemi-luminescence images were recorded on devices, on which HRP was deposited, before and after treatment with chloroform and after deposition of the semiconductor. From the images it is possible to observe that in all cases a light signal is visible, clearly indicating that the enzyme remains active and that the analyte, in this case luminol, is able to pass through the semiconductor. Further, this response demonstrates that the treatment which is necessary to device preparation keeps HRP enzyme functionality unchanged.

Figure 7:
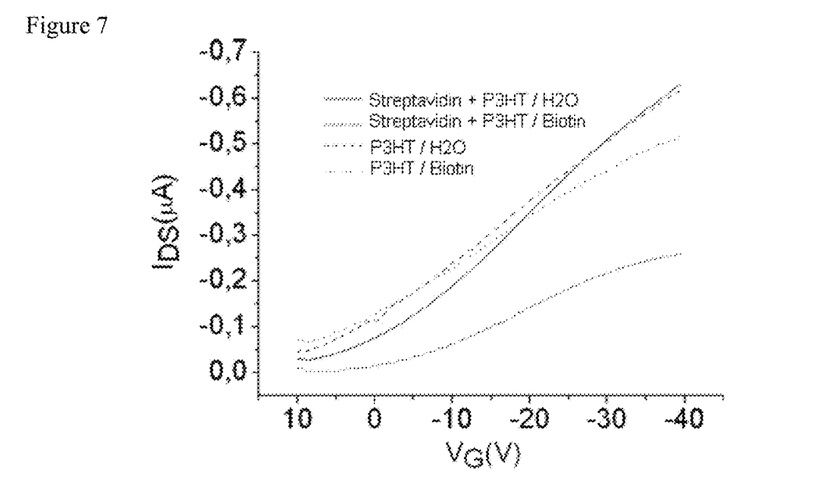
FIG. 7 shows the transfer characteristics curves obtained for FET functionalized with streptavidin exposed to water (solid line curve–streptavidin+P3HT/$H_2O$), FET functionalized with streptavidin exposed to biotin (short dashed line curve–streptavidin+P3HT/biotin). Dotted and long dashed line curves are referred to the two negative control experiments.

FET devices (FIG. 1) can be employed as biosensors since, as a result of the specific interaction of the analyte with the biological molecules immobilized as previously described, a variation of the electric OTFT properties due to changes which take place in the semiconductor deposited on the bio-active material occurs. The sensing measurements were performed measuring also in this case the transistor transfer characteristics in the absence and in the presence of the analyte. Devices, in which the biological recognition element was not immobilized (therefore made of the only P3HT), were used as negative control. Before the electric measurements the device was divided into two regions, a region was used as blank, in other words only water was added and a 10 μg/ml biotin solution in water was distributed on the other region. The transfer characteristics obtained for FETs functionalized with streptavidin treated only with water, FETs functionalized with streptavidin following the addition of biotin are displayed in FIG. 7. The other curves are measured on the negative control samples where the capture protein is not present. Streptavidin immobilization was always performed by spin-coating. The obtained results show how a much more evident current reduction is achieved in the positive sample respect to the negative one as a result of biotin addition (FIG. 7). Current reduction observed for the negative sample as a result of biotin addition can be ascribed to a weak unspecific interaction of the latter with the semiconductor. Anyway, properly optimized saturation procedures can be able to reduce such phenomenon. The lowest biotin concentration measured has been in the ppt concentration range. Seven different FETs which are present on the same chip were tested to evaluate the intra-device variability. The results reported in table 1 show the much lower variability coefficient respect to the negative control, both for the blank and after biotin addition obtained in the case of the device functionalized with the biological recognition element.

TABLE 1

In the table the mean values of the ID current calculated from the trans characteristics for VG = −39.5 after analysis of seven channels of the same device are reported. Further, the corresponding standard deviations (SD) and the percentage coefficients of variability (CV %) are reported.

| Device | Mean (=7) $I_D$ for $V_G = -39.5$ | SD | CV % |
|---|---|---|---|
| P3HT/water | 0.65 μA | 0.07 | 10% |
| P3HT/biotin | 0.39 μA | 0.04 | 10% |
| STREP + P3HT/water | 0.60 μA | 0.03 | 5% |
| STREP + P3HT/biotin | 0.28 μA | 0.01 | 4% |

Such result is quite important as it highlights how a significant improvement of sensor reproducibility occurs in presence of a specific recognition reaction. Further experiments on a high number of devices could evidence such result even with regard to the inter-device variability. Another parameter that can be used to determine the presence of the analyte is the threshold voltage Vt. In fact, values of 32.5 and 16.8 Volt respectively were obtained calculating the mean value of Vt in absence and presence of the analyte, for the different channels subjected to electric testing on a device in which streptavidin was immobilized. Instead, significant changes of Vt are not observed in the negative control. Such result could be explained considering that a change in the charge trapping properties of the FET biosensor occurs in presence of the streptavidin-biotin complex. From the discussed preliminary results it is possible to understand how the developed biosensor is perfectly capable to discriminate the presence or not of the analyte. Further, from the calibration curve it is possible to determine the concentration of the analyte which is present in the sample too. The advantages of such a device, respect to other commercially available systems, are noteworthy. In fact, beyond the possibility to develop label-free immunosensors or genosensors, namely without the employment of luminescent or enzymatic tracers, the system coupling charge transport through field effect with the bio-sensing process allows to obtain high performances mainly in terms of sensitivity and bias control. Further, the response of these devices is electronic and then immediately available through a proper circuit. Beyond testing the already developed devices using different proteins as negative and positive control, for example bovine serum albumin (BSA) and anti-biotin antibodies, future developments could be directed even to integrate systems of microfluidics in the device for reagent distribution and to develop multianalyte systems. In this last case biospecific probes will be immobilized in different positions of the device, and the signals coming from the different points (corresponding to the binding of the specific analyte) will be detected separately. In this way, it will be possible to determine and quantify different analytes which are present on the same sample simultaneously. The technology which will be employed will be that of the realization of a FET array. It is then possible to consider the development of a new platform using the electronic sensors proposed in this patent employing different biological layers also in array (matrix) configuration. Such system would allow the detection of a multianalyte system and the manufacturing of these devices could be performed with technologies presently employed for flexible electronics on a large scale. This aspect is particularly important in clinical diagnosis and in "Point Of Care" monitoring, in fact the devices to be developed could be used for the simultaneous detection of a groups of analytes related to a particular pathology. Further, disposable devices could be realized too, such format will allow to overcome the problem of biosensors regeneration, furthermore, it will avoid the risk of cross-contamination between different samples and the danger of contamination linked to the handling of infected clinical samples.

Figure 8:
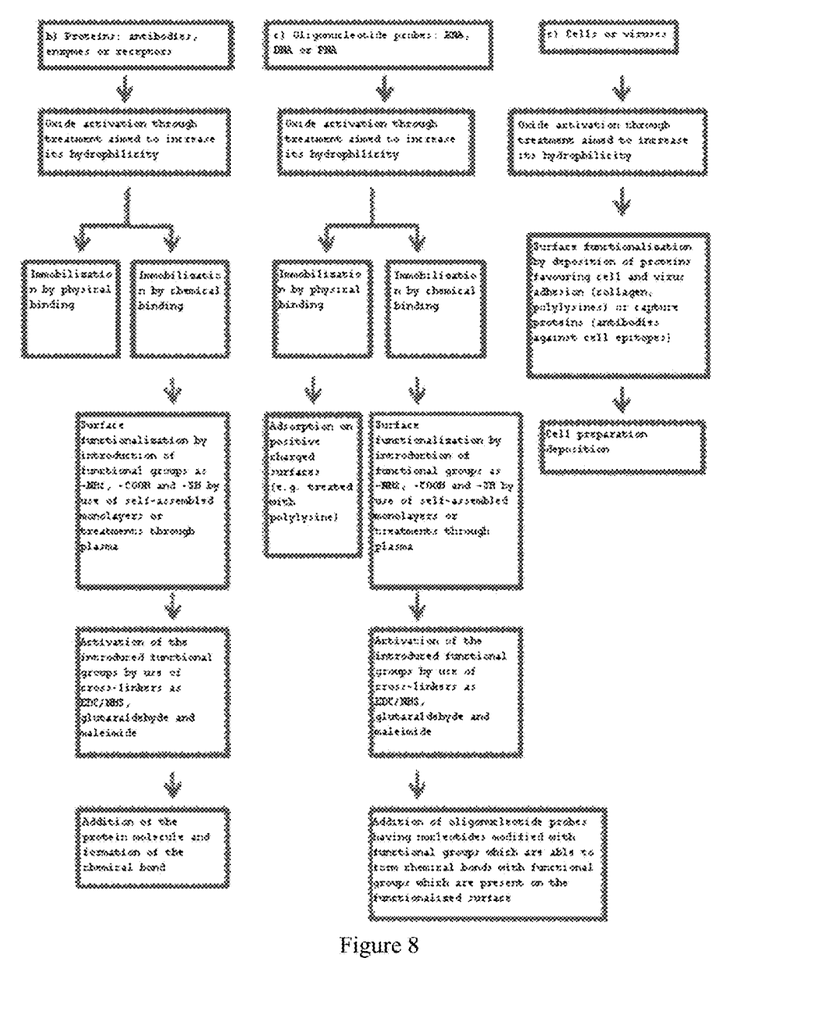
FIG. 8 depicts a deposition of biological recognition elements.

The methods for FET sensors realization with other proteins classes mentioned at point (b) as well as with the biological systems of which at points (d), (e) or (f) are depicted in FIG. 8.

The produced experimental evidences demonstrate that:

Sensor 1: the FET employing the layer (a) displays field-effect and can work as a sensor of anaesthetics. The methods adopted for the realization of sensor 1 are readily extendible to the realization of a sensor comprising the biological system (c) which includes anyone of the proteins listed at point (b) or (f).

Sensor 2: the sensor employing a layer with one of the proteins listed at point (b), in particular streptavidin, displays current amplification and works as a sensor of biotin. The methods adopted for the realization of sensor 2 are readily extendible to FETs realized with the other protein classes mentioned at point (b) as well as with the biological systems described at points (d), (e) or (f).

Both sensors can provide performances in line with the requirements of possible industrial applications.

The FET sensors here proposed can be also used for the realization of a platform employing different biological layers (one for each different device) in an array or in a matrix configuration for the detection of a multianalyte system. The array can be realized by technologies employed in flexible electronics on a large scale.

The invention claimed is:

1. A transistor comprising:
a conductive layer, a dielectric layer and an organic semiconducting layer,
a layer of biological material deposited directly on a surface of said dielectric layer,
said organic semiconductor layer deposited on top of said layer of biological material, said layer of biological material specifically interacts with an analyte and is located between said dielectric layer and said organic semiconductor layer, and
said organic semiconductor layer pervious to the analyte to which the transistor is exposed during operation.

2. The transistor according to claim 1, wherein said layer of biological material comprises:
single or double layers of phospholipids;
layers made of proteins including one of receptors, antibodies, ionic channels or enzymes;
single or double layers of phospholipids with inclusion or anchoring of proteins comprising one of receptors, antibodies, ionic channels and enzymes;
layers made of oligonucleotide probes including DNA, RNA or PNA;
layers made of cells or viruses; and
layers made of synthetic receptors, said synthetic receptors comprising molecules or macromolecules similar to biological receptors for reactivity with the analyte.

3. The transistor according to claim 1, wherein said layer of biological material is covalently bound or attached by physical adsorption or by spin-coating to the dielectric.

4. The transistor according to claim 1, wherein said organic semiconducting layer comprises a "p" or "n" -type organic semiconducting deposited by screen printing.

5. The transistor according to claim 1, wherein said organic semiconducting layer is selected from an organic or a carbon allotrope based material.

6. The transistor according to claim 1, wherein the organic semiconducting layer is deposited by spin-coating drop-casting, or by thermal evaporation.

7. The transistor according to claim 1, wherein the dielectric layer is an organic or an inorganic insulator material endowed with a high dielectric constant.

8. The transistor according to claim 1, wherein deposition of source drain, and gate contacts, occurs by thermal evaporation or sputtering of metals including gold, platinum, silver or aluminium through a shadow mask or defined by photolithographic techniques.

9. The transistor according to claim 1, further comprising contact electrodes made of a conducting polymer material.

10. The transistor according to claim 8, wherein the source and drain contacts are separated by a space ranging between 1 μm and 500 μm.

11. The transistor according to claim 1, wherein the conductive layer is either solid comprising silicon or glass or is a flexible material comprising plastic or fabric.

* * * * *